United States Patent [19]

Kofsky et al.

[11] 4,177,819
[45] Dec. 11, 1979

[54] MUSCLE STIMULATING APPARATUS

[76] Inventors: Harvey I. Kofsky, 3250 Ellendale Ave., Apt. 408, Montreal, Quebec, Canada, H3S 1W4; Arthur Levine, 5718 Rand Ave., Montreal, Quebec, Canada, H4W 2H7

[21] Appl. No.: 891,817

[22] Filed: Mar. 30, 1978

[51] Int. Cl.$^2$ ............................................. A61N 1/36
[52] U.S. Cl. ..................................... 128/422; 128/908; 128/423 R
[58] Field of Search ................ 128/2.1 P, 419 R, 421, 128/422, 423 R

[56] References Cited

U.S. PATENT DOCUMENTS

| | | | |
|---|---|---|---|
| 2,823,678 | 2/1958 | Luftman et al. | 128/422 |
| 3,050,695 | 8/1962 | Duvall | 128/421 |
| 3,077,884 | 2/1963 | Batrow et al. | 128/423 |
| 3,478,744 | 11/1969 | Leiter | 128/423 |
| 3,489,152 | 1/1978 | Barbara | 128/422 |
| 3,645,267 | 2/1972 | Hagfors | 128/421 |
| 3,718,132 | 2/1973 | Holt et al. | 128/421 |
| 4,068,669 | 1/1978 | Niemi | 128/419 R |
| 4,102,348 | 7/1978 | Hihara et al. | 128/422 |

Primary Examiner—William E. Kamm
Attorney, Agent, or Firm—Schwartz, Jeffery, Schwaab, Mack, Blumenthal & Koch

[57] ABSTRACT

The disclosure teaches an electronic apparatus for stimulating the muscles of a patient by disposing electrodes on the outer surface of the patient in the vicinity of the muscles. The stimulating wave consists of a composite signal comprising bursts of a sine wave, having a frequency greater than 500 Hz, and preferably in the range of 2000–3000 Hz, modulated by a signal at a frequency less than 500 Hz, and preferably in the range of 40–60 Hz. The bursts are applied for 2–20 second periods separated by 2–50 second rest intervals. The apparatus includes safety circuits which sense the current to the electrodes and turn off the stimulating waves on detection of a no load or overload condition. The apparatus also includes a power amplifier with a gain control and a switch associated with the gain control such that, if, at the beginning of any treatment, the gain control is not set to zero, stimulating waves will not be applied.

3 Claims, 14 Drawing Figures

MUSCLE STIMULATING APPARATUS

BACKGROUND OF THE INVENTION

1. Field of the Invention

This invention relates to an electronic muscle stimulator apparatus. More specifically, this invention relates to such an apparatus utilizing a high frequency sine wave pulse modulated at a lower frequency as the muscle stimulating wave form.

2. Statement of the Prior Art

It is known in the art to use electronic circuitry for medical instrumentation as illustrated in, for example, U.S. Pat. Nos. 3,718,132 — Holt et al; 3,650,277 — Sjostrand et at; 4,014,347 — Halleck et al; 4,019,519 — Geerling; 3,255,753 — Wing; 3,946,745 — Hsiang-Lai et al and 3,521,641 — Farensbach.

It is also known in the art to use such electronic instrumentation for the purpose of muscle stimulation as discussed in U.S. Pat. Nos. 3,589,370 — McDonald; 3,472,233 — Sarbacher; 3,516,413 — McDonald et al and 3,518,996 — Cortina.

The prior art devices use various wave forms for producing the stimulating waveforms, and it has been found that they are painful and uncomfortable. In addition, with the prior art devices there is irritation and burns on the skin. Nor do the prior art devices provide any safety devices to ensure the safety of the patient in all respects.

SUMMARY OF THE INVENTION

It has been found that pain can be reduced and skin burns and irritation eliminated by use of a sinusoidal stimulating wave form.

The frequency of the sine wave should be greater than 500 Hz and preferably in the range of 2000 Hz-3000 Hz. In a preferred embodiment, the frequency is 2500 Hz.

The stimulating wave form should be provided in bursts at a rate less than 500 Hz, preferably in the range of 40-60 Hz, and preferably 50 Hz.

Safety features will ensure that the apparatus can be restarted only when the gain control is set to zero gain.

In accordance with the invention, electronic apparatus for stimulating the muscles of a patient by disposing electrodes on the outer surface of the patient in the vicinity of the muscles, comprises: means for generating a stimulating wave for predetermined time periods separated by predetermined time intervals; said stimulating wave comprising a sinusoidal signal at a first frequency greater than 500 Hz; means for generating bursts of said signal at a rate determined by a second, lower frequency; and means connecting said signal to said electrodes.

The apparatus preferably includes means for protecting the safety of the patient, said safety means comprising: a sensor for sensing signal flow to the electrodes; control means, connected to the output of said sensor, to turn said system off when it senses either a no load or an overload condition.

The apparatus will also include a power amplifier for amplifying the stimulating wave, and gain control means for said power amplifier; said safety means further comprising: switch means, associated with said gain control means, for preventing said power amplifier from being restarted when said gain control is not set at zero gain.

The apparatus may further comprise means for varying the amplitude of said signal from zero, at the start of each period, to its full amplitude, and from the full amplitude to zero at the end of each period.

BRIEF DESCRIPTION OF THE DRAWINGS

The invention will be better understood by an examination of the following description, together with the accompanying drawings, in which.

DETAILED DESCRIPTION OF THE DRAWINGS

It has been found that the stimulating waveform should not be continuously applied, but rather, should be applied in 20-20 second ON periods separated by 2-50 second OFF intervals. In addition, it has been found that, in each ON period, the muscle stimulating waveform, rather than being applied full force at the beginning of each period, may be gradually increased from a small or zero amplitude to its full amplitude. In a like fashion, the stimulating waveform, rather than being abruptly removed at the end of a period, may be gradually decreased to zero just before the OFF interval.

The circuit in accordance with the invention includes, in addition to other features, means for automatically implementing the above three features.

Figure 1:
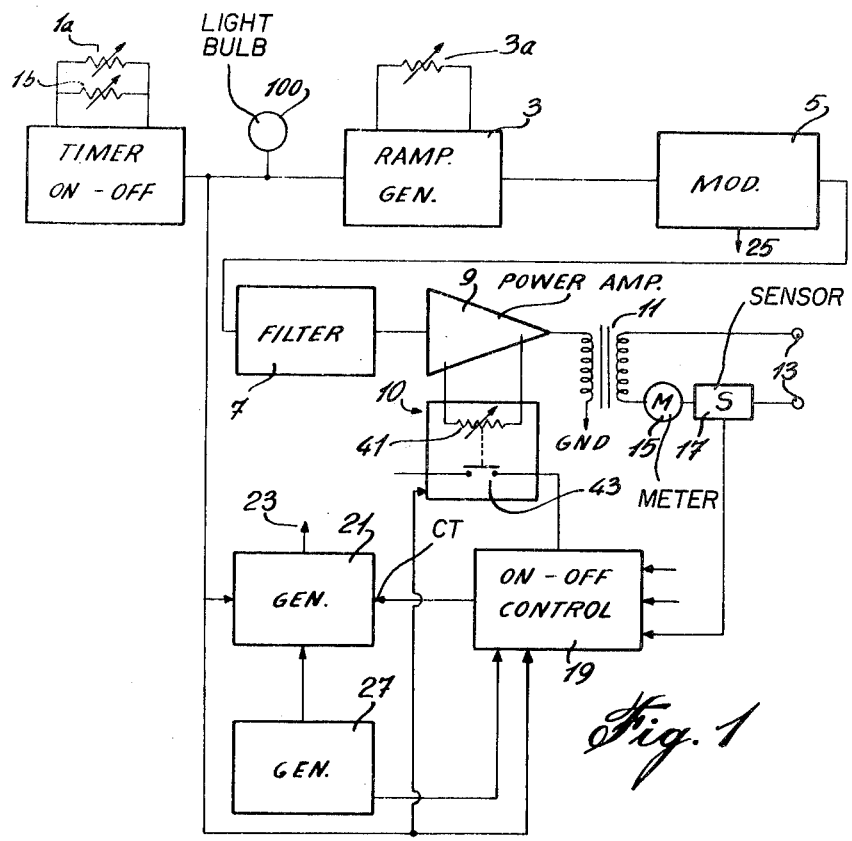
FIG. 1 illustrates, in block diagram form, one embodiment of the invention.
Figure 2A:
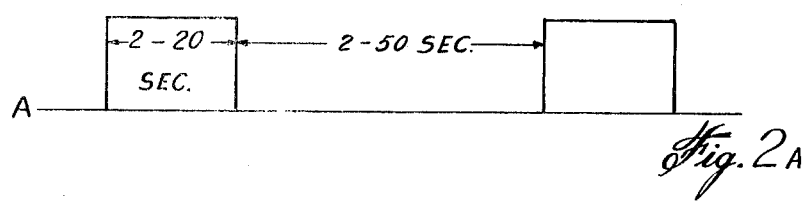
FIGS. 2A to 2G shows wave forms at different points in the circuit of FIG. 1.

Referring now to FIG. 1, timer 1 sets the ON period and the OFF interval. As seen in FIG. 2A, the ON period is adjustable from 2 to 20 seconds by adjustment means 1a which is schematically illustrated in FIG. 1 as a variable resistor. The OFF interval is adjustable from 2-50 seconds by adjustment means 1b shown in FIG. 1 as a variable resistor. As will be obvious, the timing periods and intervals could be adjustable by means other than variable resistors.

Figure 2B:
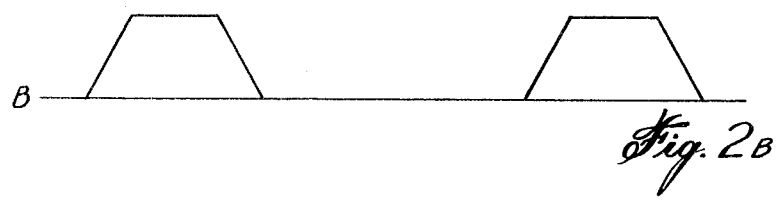

The timer 1 controls the operation of ramp generator 2. As seen in FIG. 2B, an upward ramp is generated at the beginning of each ON period, and a downward ramp is generated at the end of each ON period. The slope of the ramp is adjustable by means of slope control 3a, which is here schematically represented as a variable resistor.

As will be seen, the ramp generator ensures a gradual increase and decrease in the stimulating waveform applied to the patient. As is readily apparent, the ramp generator is only one approach for implementing the gradual increase and decrease in an automatic form.

The output of the ramp generator is applied to one terminal of modulator chopper 5, and the output of the chopper is applied to the input terminal of filter 7, which is either low pass or band pass at the frequency of generator 27 to produce a low distortion sine wave. The output of the filter is then fed to power amplifier 9, which includes gain control means 10 to be discussed below, and the output of the amplifier is fed, via output transformer 11, to electrode terminals 13. The transformer isolates the patient from ground and steps up the voltage to drive the patient load to 100 mamps maximum.

Included in one of the leads to the electrode terminals are a meter 15, which indicates the level of the output, and an isolated sensor 17 whose function will be described below.

The modulating input 25 of the chopper 5 is fed from the output 23 of frequency generator 21. The frequency of 21 is greater than 500 Hz, preferably in the range of 2000–3000 Hz, and preferably 2500 Hz. A low frequency generator 27 is connected to a START/STOP terminal of generator 21, and the frequency of 27 is less than 500 Hz and preferably of the order of 40–60 Hz, but preferably 50 Hz.

Figure 2C:
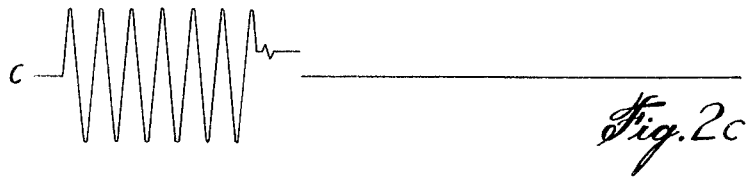
Figure 2D:
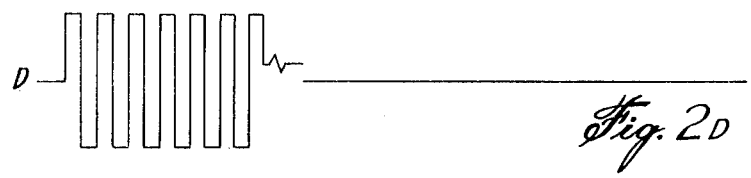
Figure 2E:
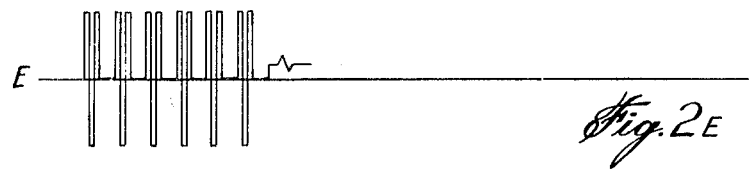

In FIG. 2, the output of generator 21, as shown specifically in FIG. 2C, is a 2000–3000 Hz signal, and the output of generator 27 is, as shown specifically in FIG 2D a 40–50 Hz signal. As the output of 27 is applied to the START/STOP terminal of 21, 27 will control the operation of 21. In this specific embodiment, the positive half of 27 will turn 21 on, and the negative half will turn it off. Thus, the output of 21, as controlled by 27, is, as shown in FIG. 2E, bursts of 2000–3000 Hz at a rate of 40–60 Hz.

This output is applied to the modulating terminal 25 of modulator 5 so that the signal of FIG. 2B is modulated by the output of 27 and will be bursts of 2000–3000 Hz at a 50 Hz rate having a rising and falling amplitude in, respectively, the zones of the upward going and downward going ramps. Between the ramps, the amplitude of the signal will, of course, be constant.

Figure 3:
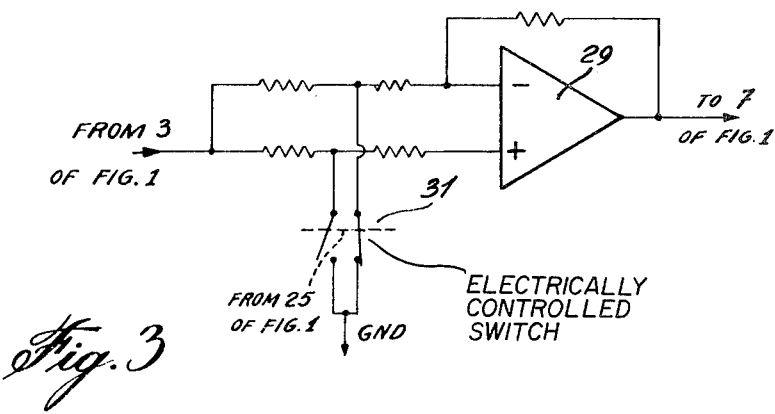
FIG. 3 is a circuit diagram of one embodiment of the modulator.
Figure 2F:
Figure 2G:

In order to produce a positive and negative going signal at the output of 5, such as shown in FIG. 2F, a circuit such as shown in FIG. 3 may be used. In FIG. 3, 29 is an operational amplifier having plus and minus terminals as indicated. 31 is an electrically controlled switch which switches the input from 3 of FIG. 1 to either the positive or negative terminals (by connecting the other signal to ground), and the movement of the switch is controlled by the output from generator 21. Thus, the output of 29 will alternate from positive to negative at the rate of and in synchronism with the output of generator 21. When there is no input from 21, both legs of switch 31 are connected to ground so that there is no output from 5.

Figure 4:
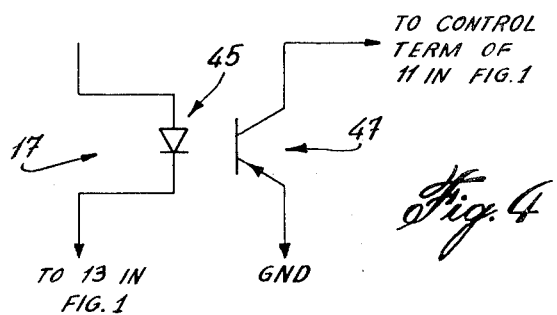
FIG. 4 is a circuit diagram of one embodiment of the sensor.

As seen in FIG. 1, the leads attached to the patient are isolated from the remainder of the circuit by transformer 11. In order to maintain the isolation, it is necessary that sensor 17 should also be isolated. In one embodiment, as illustrated herein, the sensor comprises an optically isolated circuit as shown in FIG. 4. In FIG. 4, 45 is a LED and 47 is a light sensitive transistor. When current flows through 45, it will cause the LED to emit light and activate the transistor 47. When no current flows through the LED, 47 will not be activated and it will therefore not provide an output. The intensity of the light emitted by the LED, and therefore the intensity of the output of 47, will be a function of the amplitude of the current through the LED, so that it is possible to detect both an overload and a no load condition with this sensor. At the same time, as the LED is not connected to circuit ground, and as this is the only part of the sensor which is in circuit with the patient, the patient remains isolated from the remainder of the circuit.

The control circuit 19 (see FIG. 1) comprises means for preventing a stimulating wave from being applied to electrodes 13 on detection of an overload or no load condition, as well as when the gain of the amplifier is not set to zero at the beginning of a treatment. The gain control 10 is shown in FIG. 1 as a variable resistor 11 ganged to a switch 41. This type of gain control is well known and is one in which the means for varying the resistance and the means for switching the switch are mounted on the same shaft. Such a gain control is in common use as the volume control-ON/OFF switch in radio and TV sets.

Figure 5:
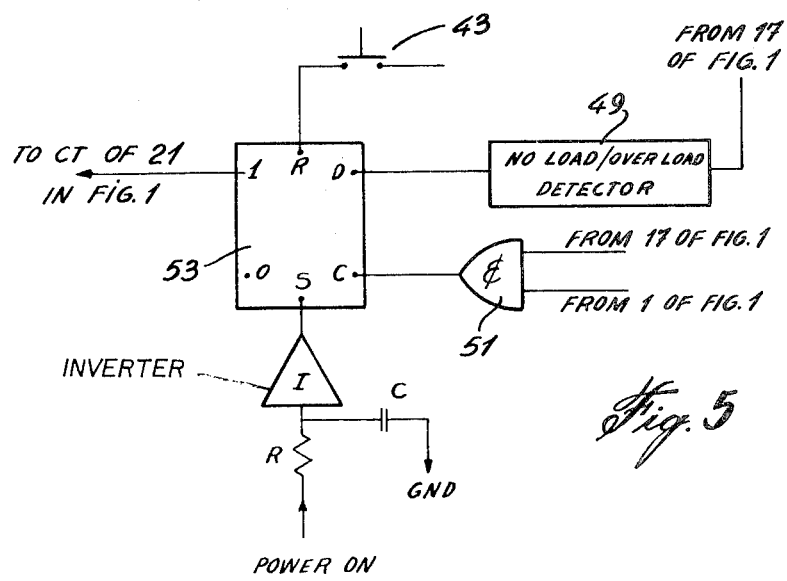
FIG. 5 is a circuit diagram of one embodiment of the logic circuit.

Referring to FIG. 5, the control circuit 19 comprises a no-load/over-load detector 49 which merely detects when the current is zero and when it exceeds a predetermined maximum, and provides an output signal under both these conditions. The logic circuit also includes AND gate 51, and the outputs of both 49 and 51 are fed to terminals D & C respectively of D-type flip-flop 53. Detector 49 is fed from sensor 17 in FIG. 1, and 51 is fed from both 27 and 1 of FIG. 1 for reasons discussed below.

The 1 output terminal of 53 is fed to the control terminal CT of 21 such that, when 1 is high, 21 is turned off. The set terminal S of the flip-flop is fed from the power ON switch of the system, through inverter I (the inverter is required in view of the required logic levels), and the reset terminal R is connected to switch 43. When power is first turned on, the flip-flop is set so that the output at 1 is high and 21 is turned off. Thus, a stimulating wave, at this moment, is not applied to electrodes 13 as there is no signal to the modulator, and therefore no signal to the power amp 9.

The level at the input of I will discharge through capacitor C at a rate determined by the factor of C and the value of resistor R, and when it falls below a given level, then it is possible to set the flip-flop. It is noted that the flip-flop will not automatically set when the level falls, it just becomes possible to set it.

If switch 43 is closed, then flip-flop 53 will be reset when the level at I falls below the given level, so that output 1 will go low, and 21 will turn on. At this point, if switch 43 is opened, the state of the flip-flop will not change, and 21 will remain on.

If an overload or no load condition is now detected at the same time that 51 is receiving an input from 1 and 27, the flip-flop will once again be set so that 21 is turned off. The reason for the gate 51 is to ensure that 21 is not turned off in each interval as a no load condition is always sensed there. It is only necessary to stop the stimulating waves when there is a no load condition during an on period.

As can be seen, flip-flop 53 can be reset only by closing switch 43. As this can happen only when the gain of the amplifier is zero, 21 can be restarted only by setting the gain to zero.

With the variable resistor gain control, it is possible to vary the gain of an amplifier during an off interval. This is undesirable, as, if the gain is low in one period, and is raised during an off interval to come on high in the next period, the abrupt change can be uncomfortable for the patient. Also, the gain should be raised while the muscles are being stimulated so that the patient feels the change and can react to it while it is being changed.

For this purpose, bulb 100 is provided in the system (see FIG. 1). The bulb will be turned on in each period and off in each interval, and an operator would be instructed to change the gain only when the light is turned on.

Figure 7:
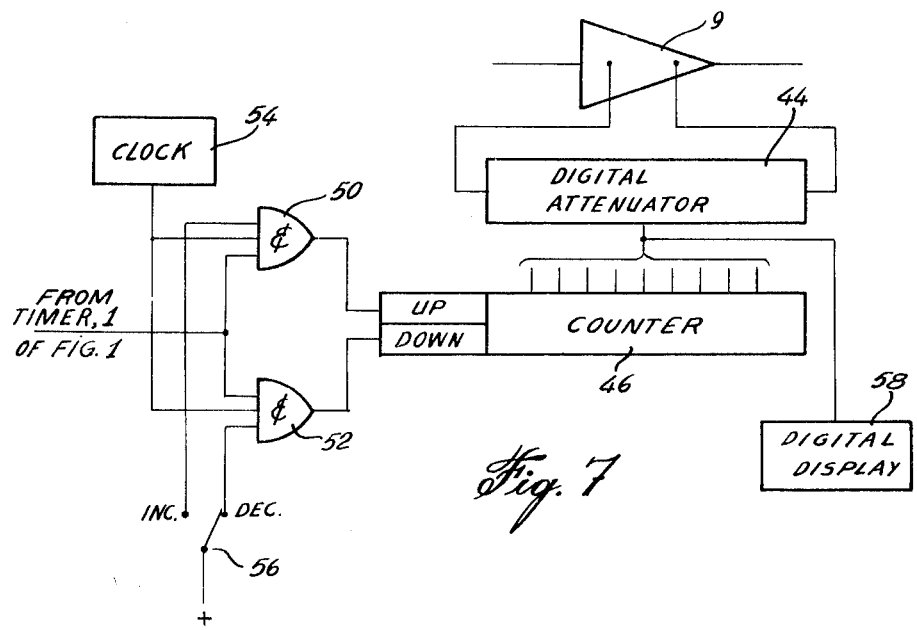
FIG. 7 illustrates a second embodiment of the invention.
Figure 8:
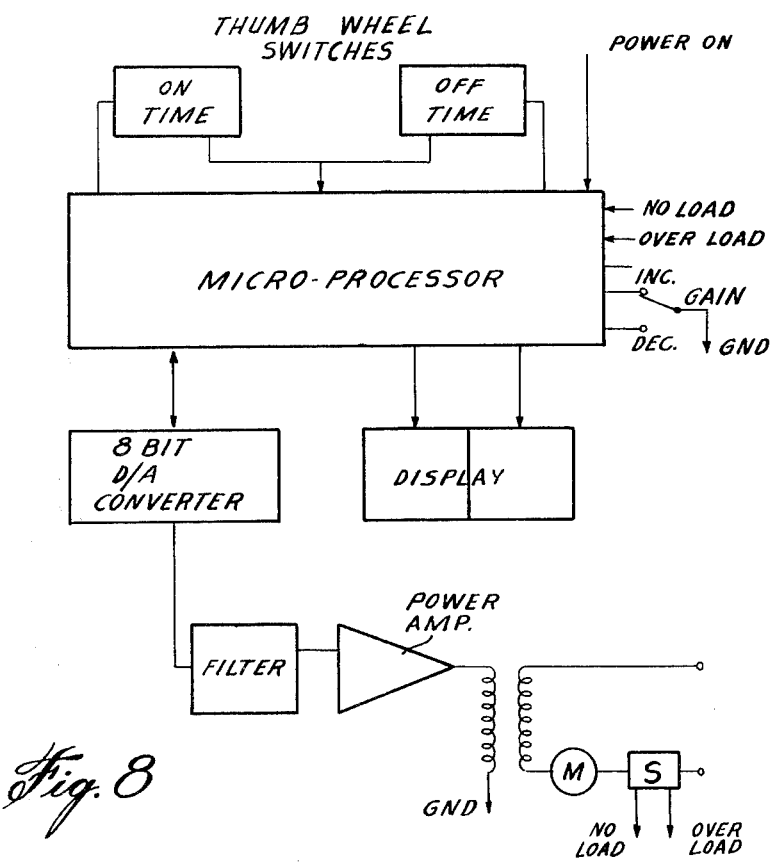
FIG. 8 illustrates an embodiment of the invention utilizing a microprocessor.

To automatically ensure that the gain is changed only during the on periods, use is made of an electronic gain control. An embodiment using such an electronic gain control is shown in FIG. 7. Referring to FIG. 7, the electronic gain control comprises digital attenuator 44 driven by counter 46. As is known, the attenuation of 44 is a function of the count on 46.

Counter 46 is driven upwardly and downwardly through AND gates 50 and 52 respectively. Gates 50 and 52 are three input gates each being fed from clock 54 at one terminal thereof, and from timer 1 of FIG. 1 at a second terminal thereof. The third terminal of gate 50 is fed from the increment position of switch 56, while the third terminal of 52 is fed from the decrease position of switch 56.

Clock 54 determines the rate at which the attenuator is varied.

As can be seen, the attenuator can be increased or decreased only during the on periods. Digital display 58 provides an output to the operator of the gain setting at any time.

In operation, the circuit of FIG. 1 works as follows:

The electrodes, connected to terminal 13, are placed on the patient as required by medical factors. The gain of the amplifier will have been turned to zero or will then be turned to zero, and the power will be turned on. The output of the modulator is applied to the low pass filter, and the output of the filter is a low distortion sine wave of equal duration and of the same amplitude as the duration and amplitude at the output of the modulator. The gain of the amplifier is then increased to the maximum level which can be tolerated by the patient. The amplifier is dimensioned so that, at maximum gain, the output is restricted to 100 MA.

The stimulating waveform is applied for periods of 2–20 seconds every 2–50 seconds, and the treatment is continued for periods of 2–10 minutes at a stretch. After a rest interval, a further treatment may be started.

It has been found that, with the inventive apparatus, the patient suffers a minimum of discomfort and is able to tolerate high gain treatments in a very short period of time. As the higher amplitude stimulating waves provide more effective treatment, a cure, or an increase in muscle strength, can be effected in a shorter period of time.

Figure 6:
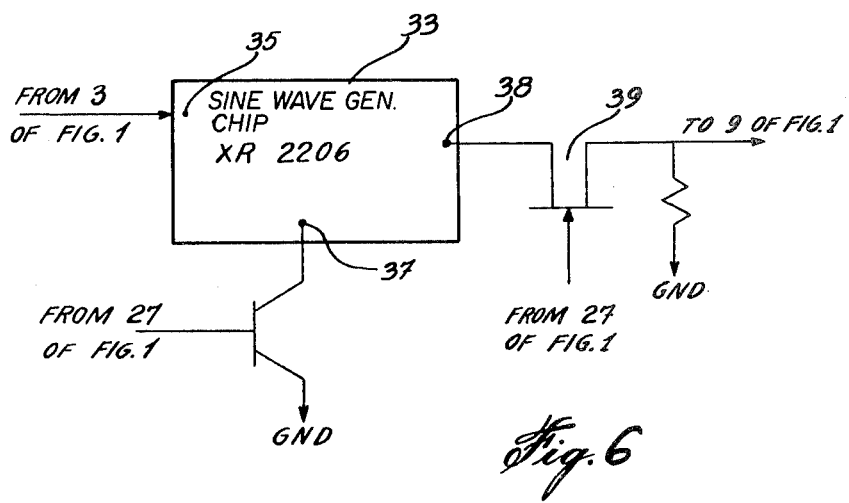
FIG. 6 illustrates a digital gain control circuit.

The circuit illustrated in FIG. 1 is only one way of producing a signal whose amplitude increases gradually at the beginning of each cycle and whose amplitude decreases gradually at the end of each cycle. A second embodiment is shown in FIG. 6. In FIG. 6, 33 is a sine wave generator chip, for example, a chip having the designation XR2206, having an amplitude control terminal 35 connected to the output of the ramp generator 3 in FIG. 1. The chip is set at a frequency between 2000–3000 Hz, and with the chip in the circuit, clocks 5, 7 and 21 of FIG. 1 are eliminated as the single chip performs the functions performed by all of the above blocks.

Because terminal 35 is connected to the output of the ramp generator, the amplitude at the output of the chip will vary during the ramp periods and be constant in between. To provide the 40–60 Hz modulation, the following alternatives are possible:

(1) Output from generator 27 can be applied to ON-/OFF terminal 37. The chip is then modulated in the same way as is generator 21 in FIG. 1. If no signal is applied to terminal 37, the output of the chip is zero. (2) A FET 39 is connected in circuit at the output terminal 38 of the chip, and the gate of the FET is connected to the output of generator 27. The FET will be alternatively conductive and non-conductive depending on the polarity of the signal applied to the gate, and it will vary at the rate of 40–60 Hz. If no signal is applied to the gate of 39, the output of the FET is zero.

The operation of this embodiment is identical to the operation of the FIG. 1 embodiment.

It is possible to replace all of the circuitry above described with a single micro-processor, and a system which implements all of the functions with a micro-processor is schematically illustrated in FIG. 6. The operation of this system is straight forward and requires no further description.

While several embodiments have been described, this was for the purpose of illustrating, but not limiting, the invention. Various modifications, which will come readily to the mind of one skilled in the art are within the scope of the invention as defined in the appended claims.

We claim:

1. Electronic apparatus for stimulating the muscles of a patient, comprising:
   electrodes disposed, in operation, on the skin surface of the patient in the vicinity of the muscles to be stimulated;
   a first generator having an output frequency of 2000 to 3000 Hz;
   means for turning said first generator on for a predetermined time period separated by predetermined intervals;
   means for gradually increasing the amplitude of said first generator output from zero at the onset of each time period, and for gradually decreasing said amplitude to zero at the end of each time period;
   said first generator having a START/STOP terminal;
   a second generator, having an output frequency of 40 to 60 Hz, connected to said START/STOP terminal to start and stop said first generator at a rate of 40 to 60 times per second;
   whereby to produce, in each of said time periods, 40 to 60 bursts per second of a 2000 to 3000 Hz signal;
   filter means receiving said 40 to 60 burst per second of said 2000 to 3000 Hz signal to produce 40 to 60 bursts per second of a low distortion 2000 to 3000 Hz sine wave; and
   means connecting said sine wave to said electrodes.

2. Apparatus as defined in claim 1 and including means for protecting the safety of the patient, said safety means comprising:
   a sensor for sensing signal flow to the electrodes;
   control means, connected to the output of said sensor, to turn said system off when it senses either a no load or an overload condition.

3. Apparatus as defined in claim 2 and further including a power amplifier for amplifying the stimulating wave, and gain control means for said power amplifier; said safety means further comprising:
   switch means, associated with said gain control means for preventing said power amplifier from being restarted when said gain control is not set to zero gain.

* * * * *